United States Patent [19]
Rogers et al.

[11] Patent Number: 5,829,977
[45] Date of Patent: Nov. 3, 1998

[54] TWO-PIECE DENTAL ABUTMENT

[75] Inventors: Dan Paul Rogers, Royal Palm Beach, Fla.; Daniel Y. Sullivan, McLean, Va.

[73] Assignee: Implant Innovations, Inc., West Palm Beach, Fla.

[21] Appl. No.: 729,869

[22] Filed: Oct. 15, 1996

Related U.S. Application Data

[60] Provisional application No. 60/005,702, Oct. 17, 1995.

[63] Continuation-in-part of Ser. No. 451,083, May 25, 1995, Pat. No. 5,725,375.

[51] Int. Cl.$^6$ ................................................. A61C 8/00
[52] U.S. Cl. ........................................... 433/172; 433/173
[58] Field of Search ................................... 433/172, 173, 433/174, 175, 176

[56] References Cited

U.S. PATENT DOCUMENTS

| | | | |
|---|---|---|---|
| 3,958,471 | 5/1976 | Müller | 82/1 |
| 4,011,602 | 3/1977 | Rybicki et al. | 433/173 |
| 4,177,562 | 12/1979 | Miller et al. | 433/174 |
| 4,547,157 | 10/1985 | Driskell | 433/173 |
| 4,624,673 | 11/1986 | Meyer | 623/16 |
| 4,713,004 | 12/1987 | Linkow et al. | 433/174 |

(List continued on next page.)

FOREIGN PATENT DOCUMENTS

| | | |
|---|---|---|
| 2 114 323 | 10/1971 | Germany . |
| 3531389 A1 | 3/1987 | Germany . |
| 4028855 | 3/1992 | Germany ............................. 433/173 |
| 1291470 | 10/1972 | United Kingdom . |
| WO 85/02337 A1 | 6/1985 | WIPO . |

OTHER PUBLICATIONS

Adell et al., "A 15–year Study of Osseointegrated Implants in the Treatment of the Endentulous Jaw," *Int. J. Oral Surg.*, 1981, pp. 387–416.

New Bio–Esthetic™ Technique Manual, "Abutment Selection and Modification Guide," Steri–Oss Inc., 1995 (6 pages).

"EsthetiCone™ systeM Components," Undated (1 page).

"1989 Core–Vent Implant Symposium," Core–Vent Corporation, Mar. 1988 (2 pages).

*Primary Examiner*—Cary E. O'Connor
*Attorney, Agent, or Firm*—Arnold, White & Durkee

[57] ABSTRACT

A two-piece abutment system is disclosed. The first part includes a tapering inner surface which is part of a bore extending entirely through the first part. The first part includes a socket for mating with a boss or post on a dental implant. The elongated second part includes a threaded stem for engaging a threaded bore with a dental implant and a post which extends above the first part. The second part extends through the bore of the first part and is screwed into the implant. As the second part is screwed into the implant, a tapering external surface on the post of the second part frictionally locks with the tapering inner surface of the first part.

54 Claims, 11 Drawing Sheets

U.S. PATENT DOCUMENTS

| | | | |
|---|---|---|---|
| 4,738,623 | 4/1988 | Driskel | 433/173 |
| 4,772,204 | 9/1988 | Söderberg | 433/174 |
| 4,872,839 | 10/1989 | Brajnovic | 433/173 |
| 4,988,297 | 1/1991 | Lazzara et al. | 433/173 |
| 5,035,619 | 7/1991 | Daftary | 433/173 |
| 5,071,351 | 12/1991 | Green, Jr. et al. | 433/173 |
| 5,073,111 | 12/1991 | Daftary | 433/173 |
| 5,100,323 | 3/1992 | Friedman et al. | 433/173 |
| 5,104,318 | 4/1992 | Piche et al. | 433/174 |
| 5,122,059 | 6/1992 | Durr et al. | 433/173 |
| 5,125,839 | 6/1992 | Ingber et al. | 433/169 |
| 5,135,395 | 8/1992 | Marlin | 433/174 |
| 5,145,372 | 9/1992 | Daftary et al. | 433/173 |
| 5,169,308 | 12/1992 | Kvist | 433/173 |
| 5,195,892 | 3/1993 | Gersberg | 433/173 |
| 5,197,881 | 3/1993 | Chalifoux | 433/173 |
| 5,209,659 | 5/1993 | Friedman et al. | 433/173 |
| 5,286,195 | 2/1994 | Clostermann | 433/172 |
| 5,297,963 | 3/1994 | Daftary | 433/172 |
| 5,334,024 | 8/1994 | Niznick | 433/173 |
| 5,344,457 | 9/1994 | Pilliar et al. | 623/16 |
| 5,350,300 | 9/1994 | Gallais | 433/173 |
| 5,362,234 | 11/1994 | Salazar et al. | 433/173 |
| 5,362,235 | 11/1994 | Daftary | 433/173 |
| 5,368,483 | 11/1994 | Sutter et al. | 433/173 |
| 5,417,570 | 5/1995 | Zuest et al. | 433/173 |
| 5,431,567 | 7/1995 | Daftary | 433/172 |
| 5,433,606 | 7/1995 | Niznick et al. | 433/173 |
| 5,437,551 | 8/1995 | Chalifoux | 433/173 |
| 5,476,382 | 12/1995 | Daftary | 433/172 |
| 5,533,898 | 7/1996 | Mena | 433/173 |
| 5,538,426 | 7/1996 | Harding et al. | 433/172 |
| 5,547,377 | 8/1996 | Daftary | 433/172 |
| 5,564,924 | 10/1996 | Kwan | 433/173 |
| 5,588,838 | 12/1996 | Hansson et al. | 433/173 |

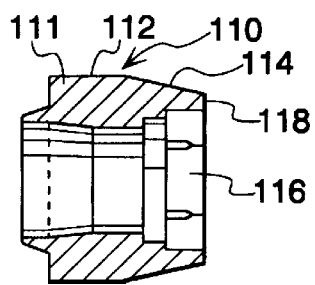 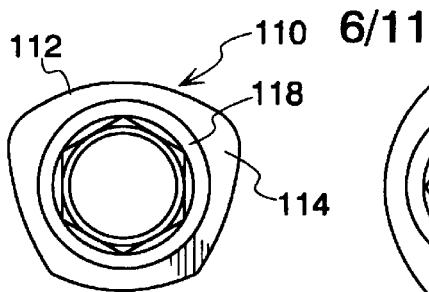 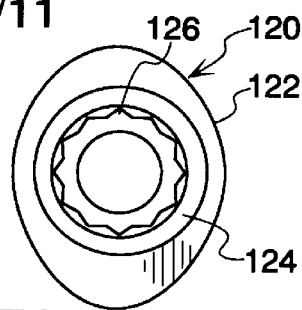
Fig. 10A   Fig. 10B   Fig. 10C
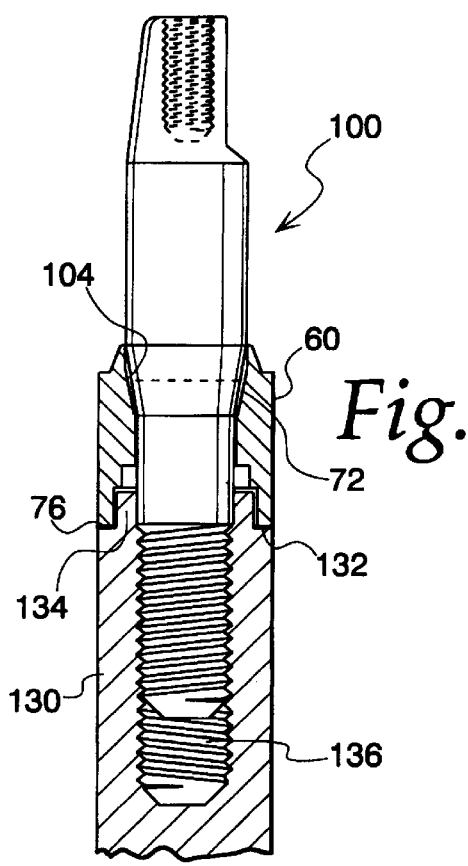 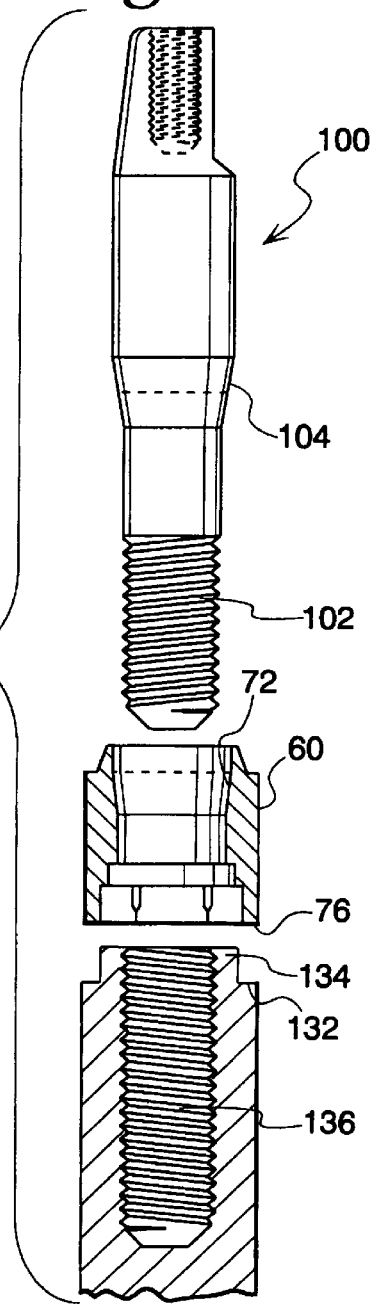
Fig. 11a   Fig. 11b

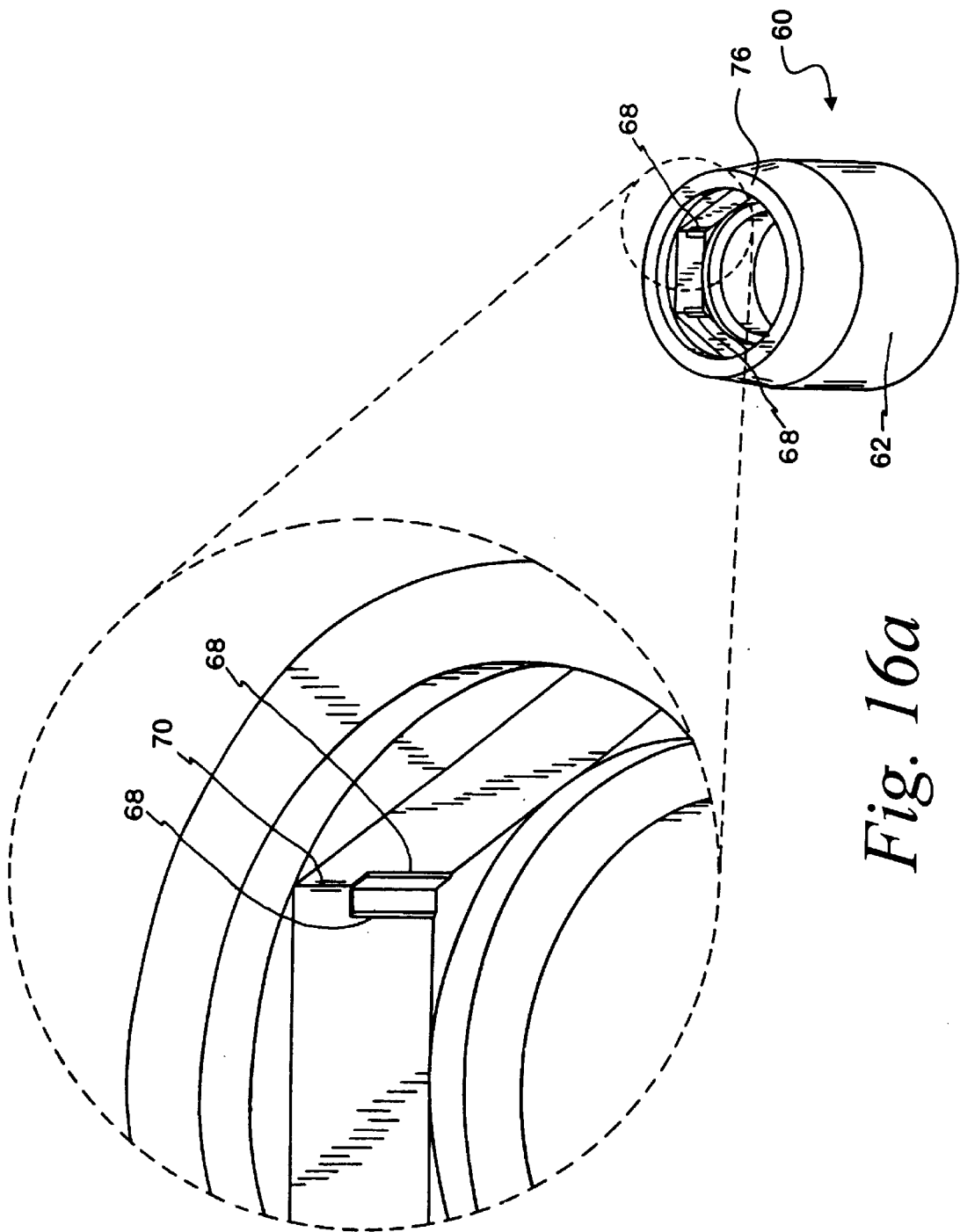

2

TWO-PIECE DENTAL ABUTMENT

CROSS-REFERENCES TO RELATED APPLICATIONS

This application is a continuation-in-part of provisional U.S. patent application Ser. No. 60/005,702 filed on Oct. 17, 1995 and U.S. patent application Ser. No. 08/451,083 filed on May 25, 1995, now U.S. Pat. No. 5,725,375.

BACKGROUND OF THE INVENTION

This specification describes, with references to the accompanying drawings, an improvement in abutments used to attach dental restorations to artificial dental roots such as dental implants. The illustrated abutment has a generally tubular first part which can be fitted through overlying gum tissue and attached non-rotationally to a dental implant. The first part provides a through-passage to a receiving bore in the implant. A second part of the abutment has an attaching stem extending through the through-passage of the first part into the receiving bore and a post protruding supragingivally through the first part from the stem. The post of the second part and the first part have respective male and female intermitting locking tapers which serve to frictionally lock the second part against turning in the first part when the stem is properly engaged in the receiving bore. Typically, the receiving bore is internally threaded and the stem is externally threaded so as to screw into the receiving bore. In use, the first part is fitted onto the implant and the threaded stem of the second part is screwed into the receiving bore until the male locking taper of the second part engages tightly in the female locking taper of the first part. In this way, the two-piece abutment is effectively attached non-rotationally to the implant.

The post of the second part may be configured to serve other functions in the dental restoration process. For example, the post may have flat side that allows it to serve as an impression coping. Additionally, the post may have means for fastening other components thereon. For example, a healing cap that encompasses the post may be attached to the post. Alternatively, an impression coping may be attached thereon. Lastly, the post may serve as a structure for supporting both a temporary or permanent dentition.

BRIEF DESCRIPTION OF THE DRAWINGS

In the accompanying drawings:

FIGS. 10A–10C illustrate alternative first parts in which the exterior surface is non-round;

FIGS. 11A–11B illustrate the assembly of the first part of FIG. 7 and the second part of FIG. 9 mounted on an implant;

FIGS. 16a–16f illustrate the first part of the two-piece abutment having anti-rotational connecting structures in the socket region.

DETAILED DESCRIPTION OF THE DRAWINGS

Figure 1:
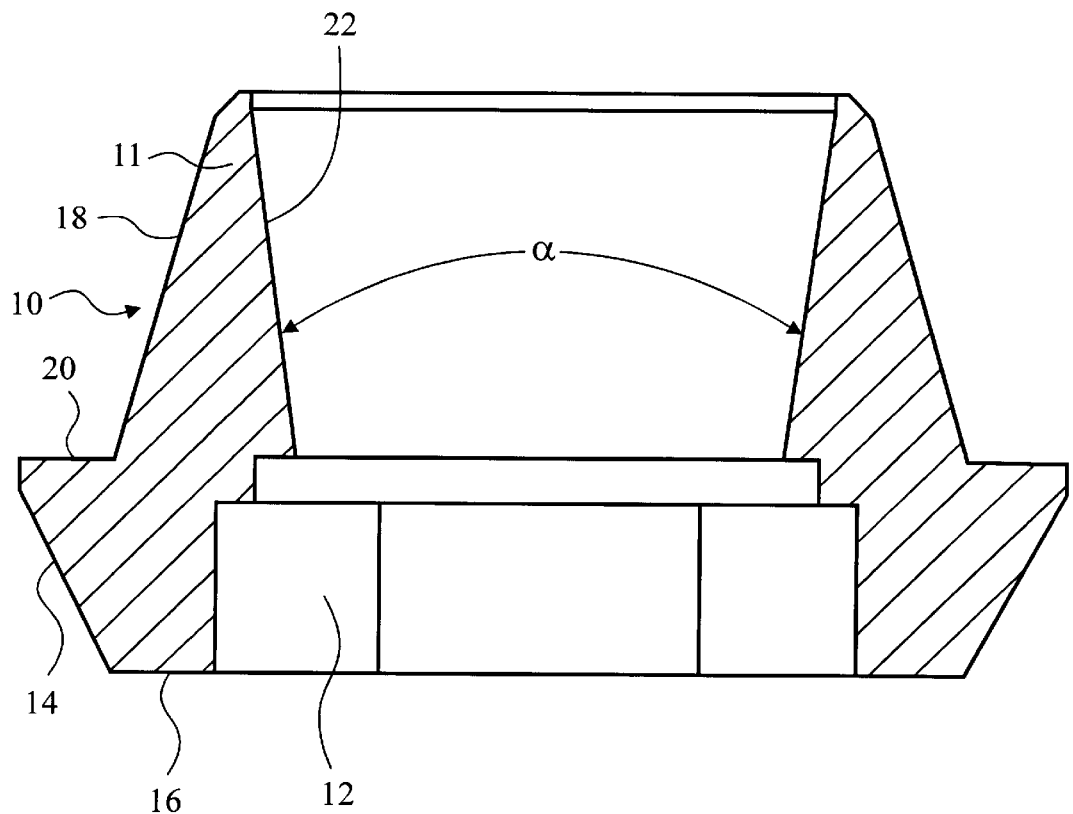
FIG. 1 shows a first part of the two-piece abutment in longitudinal cross-section.

The first part 10 shown in FIG. 1 comprises a tubular body 11 having a socket 12 at its lower section 14. The socket 12 extends upwardly into the body 11 from its lower wall 16 and has a regular polygonal (hexagonal) transverse shape for interfitting non-rotationally on a matching boss of a typical dental implant (illustrated in FIGS. 11–15). Externally, the lower section 14 of the body 11 has an expanding transverse size as it proceeds away from the lower wall 16 and an upper section 18 of contracting transverse size as it proceeds further away from the lower wall 16. Where the lower and uppers sections 14 and 18 are joined the upper section 18 is smaller transversely than the lower section 14 which provides for a shoulder 20 facing away from the implant. The upper section has a female locking taper 22 which opens into the socket 12. The female locking taper 22 and the socket 12 form a part of a bore through the first part 10. The female locking taper 22 diverges at an angle α which is generally in the range from about 5° to about 20°.

Figure 2:
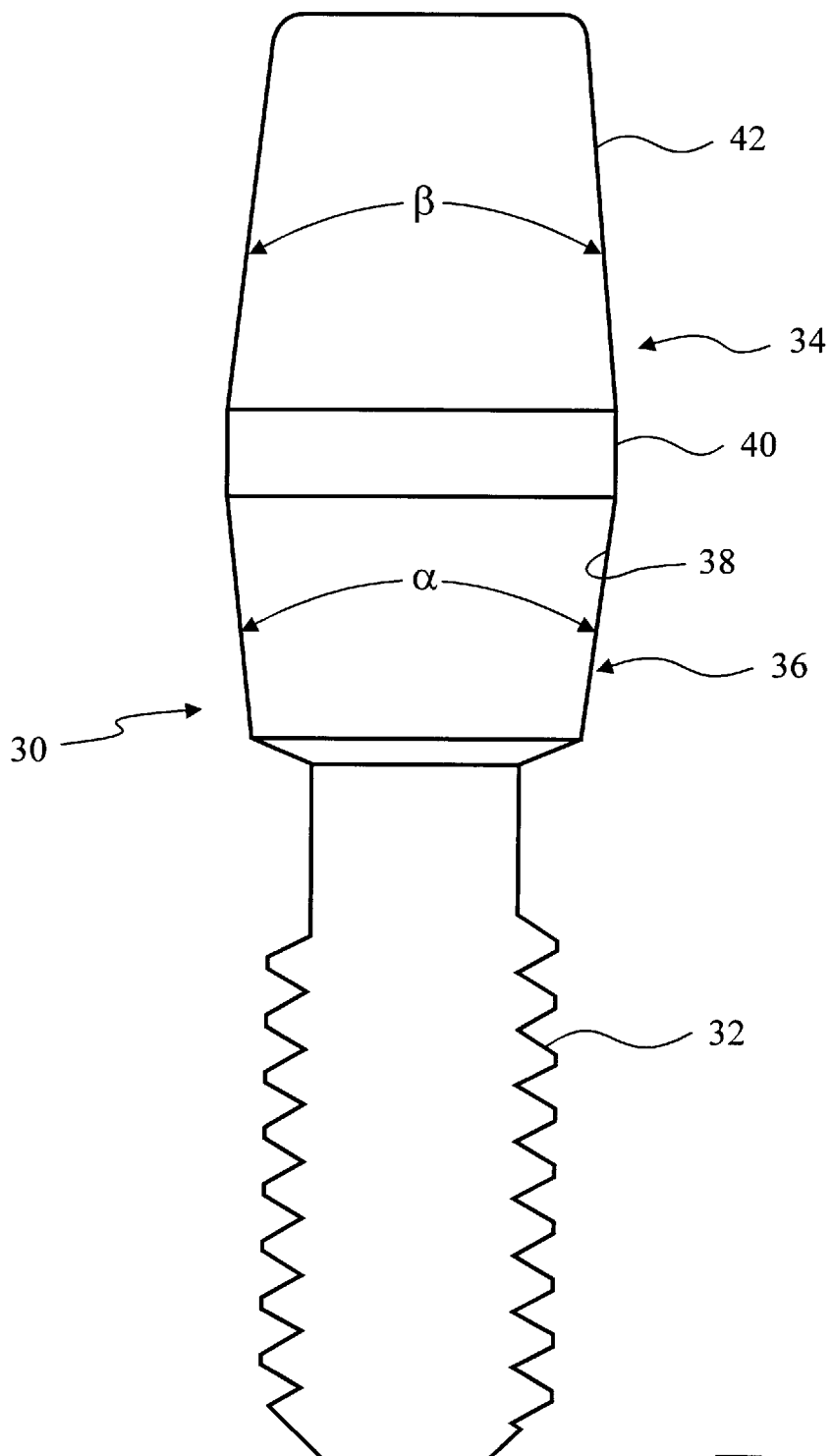
FIG. 2 is a side view of a second part of the two-piece abutment.

The second part 30 shown in FIG. 2 has a threaded stem 32 and a post 34 which is in three sections. A first section 36 has a male locking taper 38 matching the female locking taper 22 of the first part 10. Thus, angle α in the first section 36 is the same as angle α in the female locking taper 22 of the first part 10. An intermediate section 40 is generally cylindrical. A third section 42 has a contracting transverse section and tapers inwardly at an angle β which is typically in the range from about 5° to about 30°. The size of the post 34 may vary based on the patient and the function for which the second part 30 is used. For example, a second part 44 in FIG. 3 has a post with a longer intermediate section 46.

Figure 4:
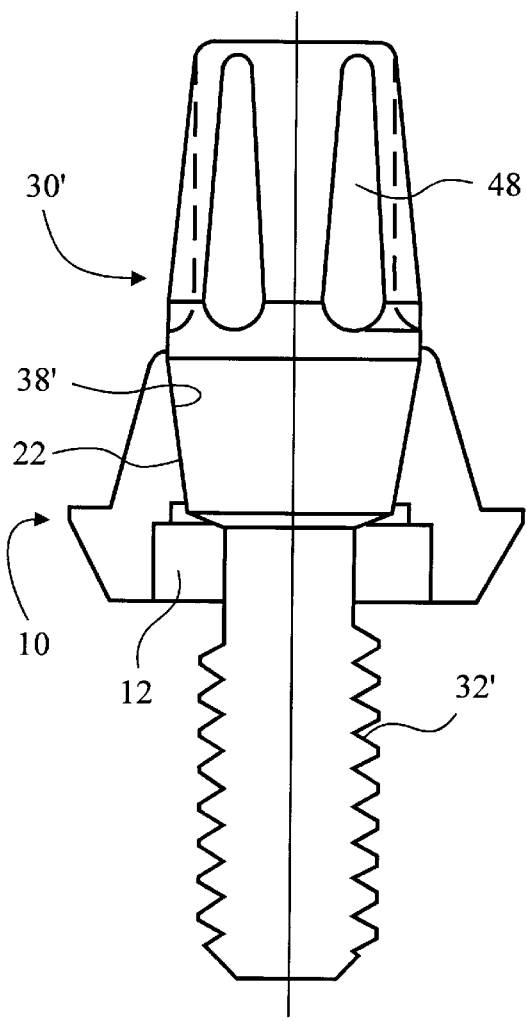
FIG. 4 is a side view of an assembly of a second part having flutes along the post and the first part of FIG. 1.

As can be seen in FIG. 4, the post extends above the first part 10 by an amount at least as large as the height of the first part 10. In some cases, as is shown in FIG. 6, the post extends above the first part 10 by an amount roughly the same as the length of the second part below the upper edge of the first part 10.

Figure 5:
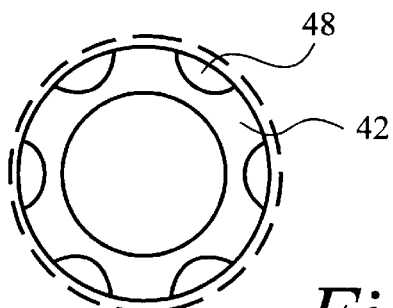
FIG. 5 is an end view of FIG. 4.

FIGS. 4–5 illustrate a second part 30' which is similar in size and shape to the second part 30 of FIG.2. However, second part 30' includes a plurality of flutes 48 where a tool (not shown) can engage and rotate the second part 30' into the first part 10 as the threaded stem 32' is screwed into a threaded bore of an implant. When the two parts 10 and 30' are assembled, as shown in FIG. 4, the locking tapers 22 and 38' engage to frictionally lock the two parts 10 and 30' against relative rotation. With the stem 32' screwed into an implant and the socket 12 non-rotationally engaged on the implant, the two-piece abutment of the invention is non-rotationally fixed to the implant.

Figure 3:
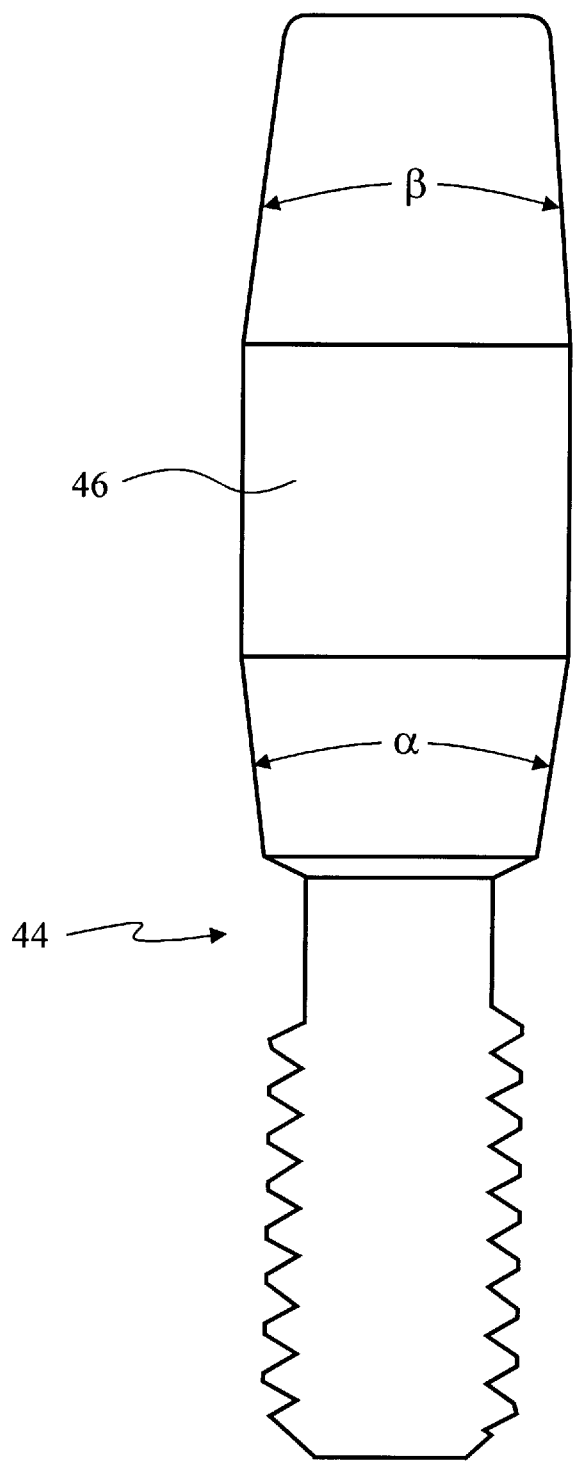
FIG. 3 is a side view of an alternative second part having a longer post.
Figure 6:
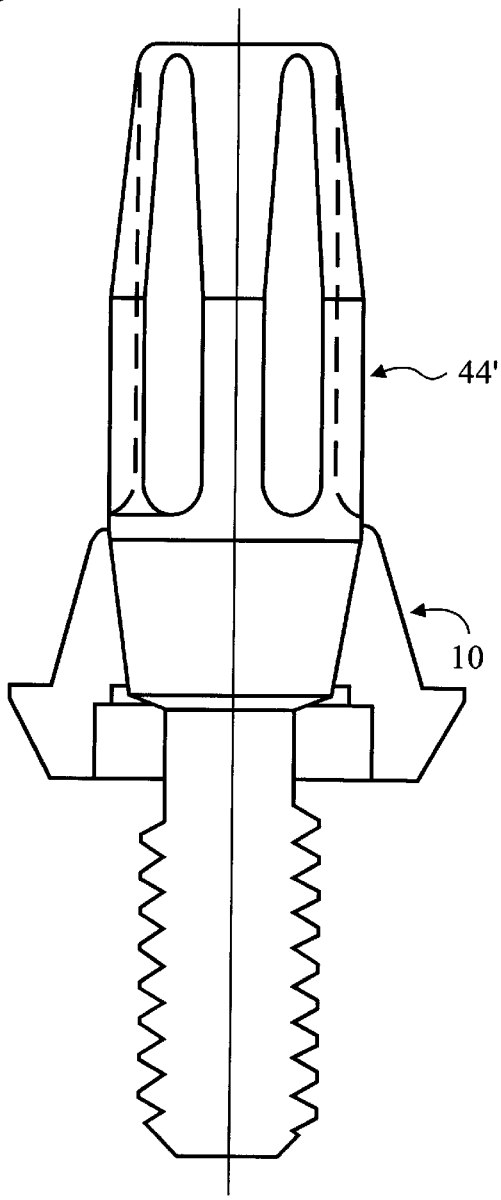
FIG. 6 is a side view of an assembly having a longer second part with flutes and the first part of FIG. 1.

FIG. 6 shows a longer second part 44' that is similar to the second part 44 which has a larger post and engages the first part 10 (FIG. 3). The male locking tapers of both second parts 44' and 30' (FIG. 4) are interchangeably the same such that both second parts 44' and 30' may be used with the same first part 10. Similarly, first parts of different external configurations may be provided as is evident in FIGS. 7 and 10 below. It will be understood that the interchangeability of components in this invention lends itself to providing components in sets that may be adapted to various dental restoration tasks depending on the needs of a particular patient. Once the two parts 10 and 30 are in their final position on the implant, the clinician can then prepare the post 34 such that it conforms to the precise height and angle of the adjacent teeth. The clinician performs this task by cutting into the surface of the post 34. In essence, the two-piece abutment system can be used in its manufactured configuration or adjusted to a unique configuration that is suited for a particular patient.

Figures 7A, 7B, 7C:
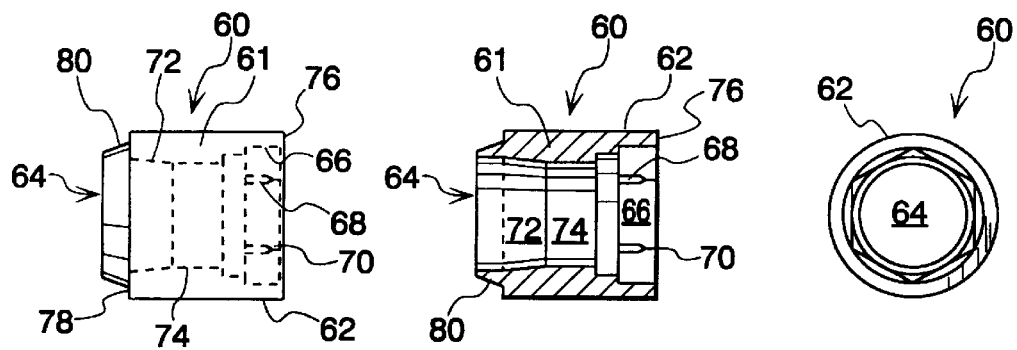
FIGS. 7A–7C illustrate an alternative first part which has a cylindrical outer surface.

FIGS. 7A–7C illustrate an alternative first part 60 which has a body 61 with a substantially cylindrical outer surface 62. A bore 64 extends through the body 61 and includes a socket region 66. The socket region 66 is polygonal (hexagonal in this case) and includes an anti-rotational structure 68 in each of its six corners 70. These anti-rotational structures 68 are discussed in detail below with reference to FIGS. 16a–16f.

The bore 64 also includes a locking taper region 72 and an intermediate region 74. The locking taper region 72 engages a correspondingly shaped male taper on a post of a second part of the two-piece abutment like second parts shown in FIGS. 8–9. The angle of the taper is typically the same as the range given for angle α in FIG. 1. Moreover, the style of the first part 10 in FIGS. 1–6 and the style of the first part 60 in FIGS. 7A–7C may be in the same dental kit such that the clinician chooses the style that is best suited for his or her patient. Preferably, the internal taper angle is the same for the first parts 10 and 60 so that same type of second part can be utilized. Additionally, a dental set may include not only different styles, but it may include different sizes of each style.

The first part 60 includes a bottom surface 76 which is adjacent the socket region 66 and engages the implant. At the other end of the first part 60, a shoulder 78 resides which provides for a surface against which another component may abut. An externally tapered region 80 is at the extremity of the first part 60.

Figures 8A, 8B:
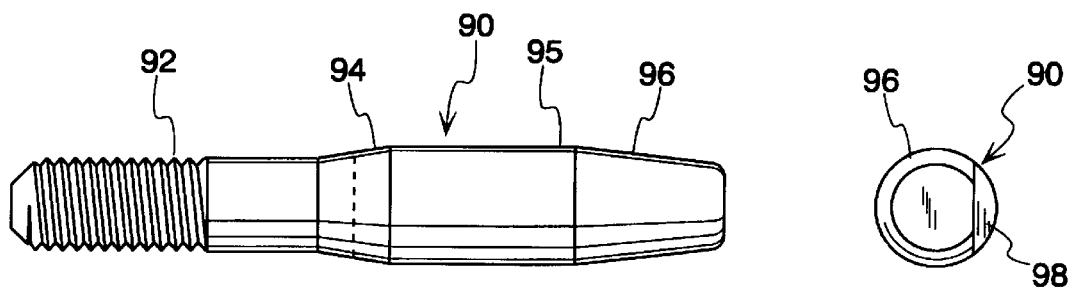
FIGS. 8A–8B illustrate an alternative second part having a flattened side on its post.

FIGS. 8A and 8B illustrate a second part 90 that is compatible with the first part 60 in FIGS. 7A–7C. The second part 90 includes a threaded shaft 92 which mates with an internally threaded bore of the implant. A male tapered portion 94 is adjacent the threaded shaft 92 and matches the locking taper region 74 of the first part 60. An intermediate portion 95 is adjacent the tapered portion 94 and is generally cylindrical. Lastly, an upper portion 96 that reduces in cross section is located at the extremity of the second part 90. As is seen only in FIG. 8B, the upper portion 96 has a flattened surface 98 which provides for a surface to grip when rotating the second part 90. The flattened surface 98 also provides for the non-rotational mating with another component encompassing upper portion 96 assuming that component includes a flat interior surface that engages the flattened surface 98.

Figures 9A, 9B:
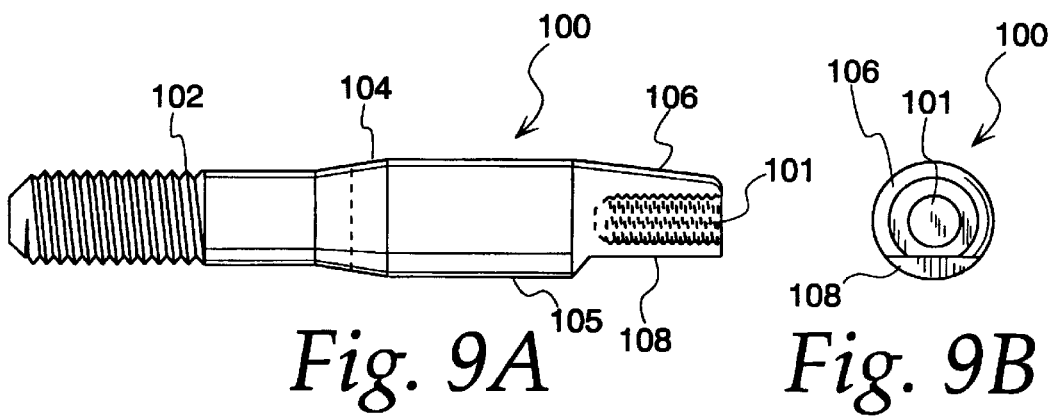
FIGS. 9A–9B illustrate an alternative second part having a threaded bore in its post.

FIGS. 9A–9B illustrate an alternative second part 100 which differs from the second part 90 in FIGS. 8A–8B only in that it contains a threaded bore 101 in its upper portion 106. The threaded bore 101 is used to attach other components to the second part 100 as will be shown in FIGS. 12–15. Thus, the threaded shaft 102, the male tapered portion 104, the intermediate portion 105, and the flattened surface 108 on the upper portion 106 are the same structures that are present on the second part 90 in FIGS. 8A–8B.

FIGS. 10A–10C illustrate yet other alternative first parts. FIGS. 10A and 10B illustrate a non-round shape to a first part 110. The body 111 has an outer surface 112 that is non-round initially but then gradually changes to round in a tapered section 114 adjacent the socket 116. Thus, the bottom surface 118 is round to mate with a cylindrical implant. By utilizing a non-round shape, the gingiva above the implant can be formed and maintained in the shape that natural tooth had in that region. Consequently, a more aesthetically pleasing prosthesis can be developed since it will emerge from the gingiva in the same contour as the natural tooth did.

FIG. 10C illustrates a first part 120 which deviates from the first part 110 of FIGS. 10A–10B in two ways. First, an oval shape is present on an exterior surface 122 of the first part 120. This oval shape also gradually changes to a round shape at the lower surface 124 so as to mate with a cylindrical implant. And, a socket 126 is present that includes the shape of a twelve-pointed star that allows the first part 120 to be mounted on the hexagonal boss of an implant in twelve orientations. It should be noted that the internal structure of the first parts 110 and 120 of FIGS. 10A–10C is the same as the previously described first parts so as to be interchangeable those devices. Expanding the dental kit to include non-round shapes offers more options to the clinician and allows him or her to select a first part that is best suited for the patient.

FIGS. 11A–11B illustrate the first part 60 of FIG. 7 and the second part 100 of FIG. 9 mounted on an implant 130. The implant 130 has an upper table 132 on which the lower surface 76 of the first part 60 mates. The socket 66 of the first part 60 captures the correspondingly shaped boss 134 on the implant 130. As the threaded shaft 102 of the second part 100 is screwed into a threaded bore 136 in the implant 130, the locking tapered surfaces 104 and 72 engage and tighten. Typically, the torque required to complete the assembly of the first and second parts 60 and 100 on the implant 120 is in the range from about 30 N●cm to about 40 N●cm. Once assembled, the two-piece abutment serves numerous functions as is described below.

Figures 12, 13:
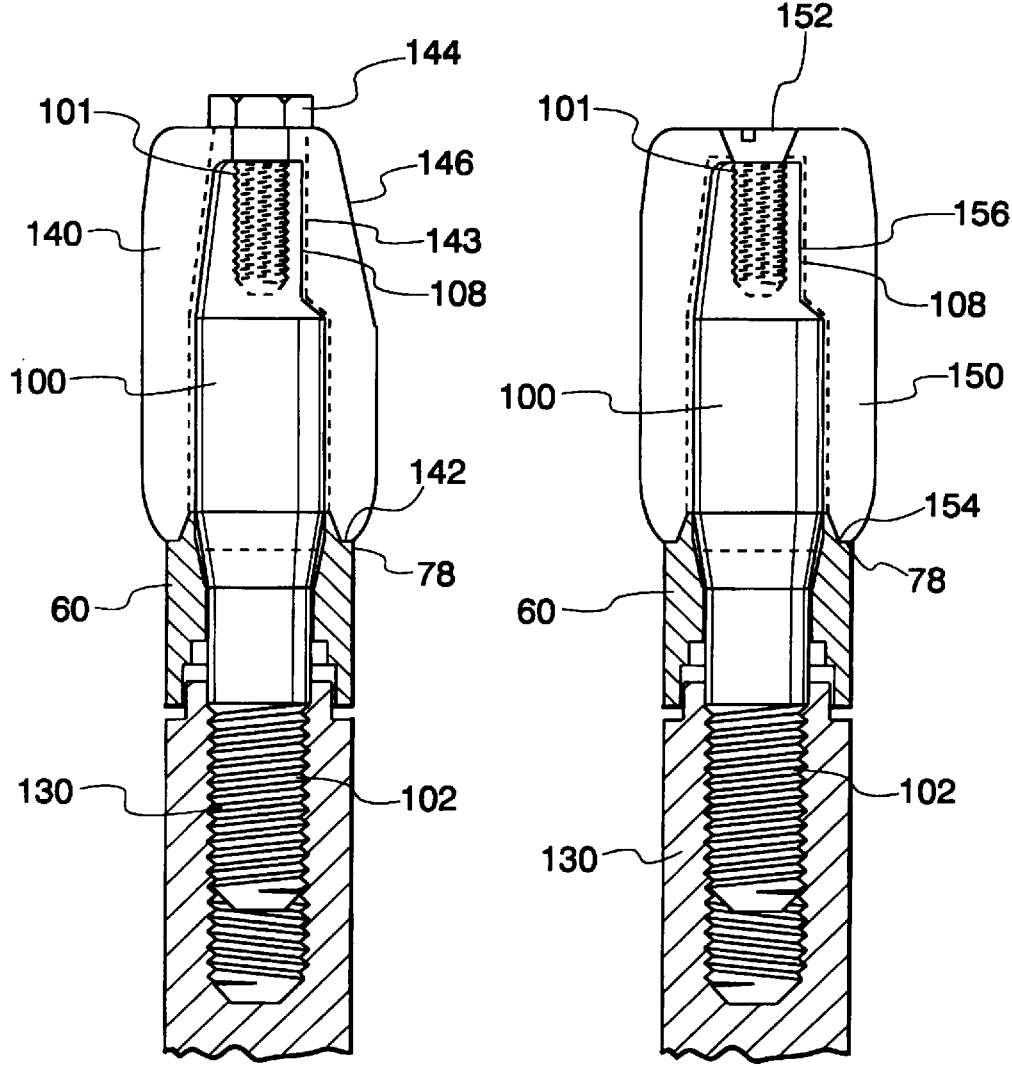
FIG. 12 illustrates the assembly of FIG. 11 with an impression coping attached to the post.
FIG. 13 illustrates the assembly of FIG. 11 with a healing cap attached to the post.

FIG. 12 illustrates an impression coping 140 fixed on the second part 100. The impression coping 140 has a bottom surface 142 which engages the shoulder 78 of the first part 60. The interior surface of the impression coping 140 has a contour that matches the contour of the exterior surface of the second part 100. Thus, the interior surface has a flat region 143 to match the external flattened surface 108 of the second part 100 to resist rotation therearound. The impression coping 140 also includes a wide-head screw 144 which threadly engages threaded bore 101 and holds the impression coping 140 on the second part 100. The impression coping 140 includes an external flat side 146 which allows for the impression coping 140 to be properly realigned within the impression material after the impression is made. Instead of one flat side 146, the coping 140 can have several surfaces for non-rotationally engaging the impression material. As shown, the impression coping 140 is a transfer coping in that after the impression is taken, the impression material is removed without the coping 140 be carried with it. The screw 144 is removed and coping 140 is "transferred" back into the impression material with the flat surface 146 being aligned with the flat surface within the cavity of the impression material. The coping 140 is then mounted on an analog of the implant 130 and the first and second parts 60 and 10 and a model of the region is made.

Alternatively, the screw 144 could be elongated with a head that extends above the impression material. After the impression material has been placed at the site, the elongated screw, which is exposed through the impression material, is unscrewed. The coping 140 would then be retained within, or "picked-up" by, the impression material when it is removed from the site. Thus, the impression coping 140 could also be used as a pick-up type impression coping.

Furthermore, the second part 100 with its flat surface 108 could itself be used as an impression coping. That is to say that the impression material can be placed directly over the second part 100. Then, after the impression material is removed, an angular registering mark is placed between the first part 60 and the second part 100 to ensure that they are realigned exactly on an implant analog when making the model to develop a permanent dentition. While the first and second parts 60 and 100 are removed, a temporary abutment could be placed on the implant. Alternatively, a second set of the first and second parts 60 and 100 having a healing cap (FIG. 13) or a temporary dentition (FIG. 15) could be placed on the implant until the original set is returned with a permanent dentition attached.

FIG. 13 illustrates a healing cap 150 that is placed over the second part 100. The healing cap 150 is held on the second part 100 by a screw 152 that threadably engages the threaded hole 101. The screw 152 is approximately flush with the upper surface of the healing cap 150. The healing cap 150 has a lower surface 154 which engages the shoulder 78 of the first part 60. The interior surface of the healing cap 150 includes a flat portion 156 that engages the flattened side 108 of the second part 100 to resist rotation of the healing cap 150 around the second part 100.

Figures 14, 15:
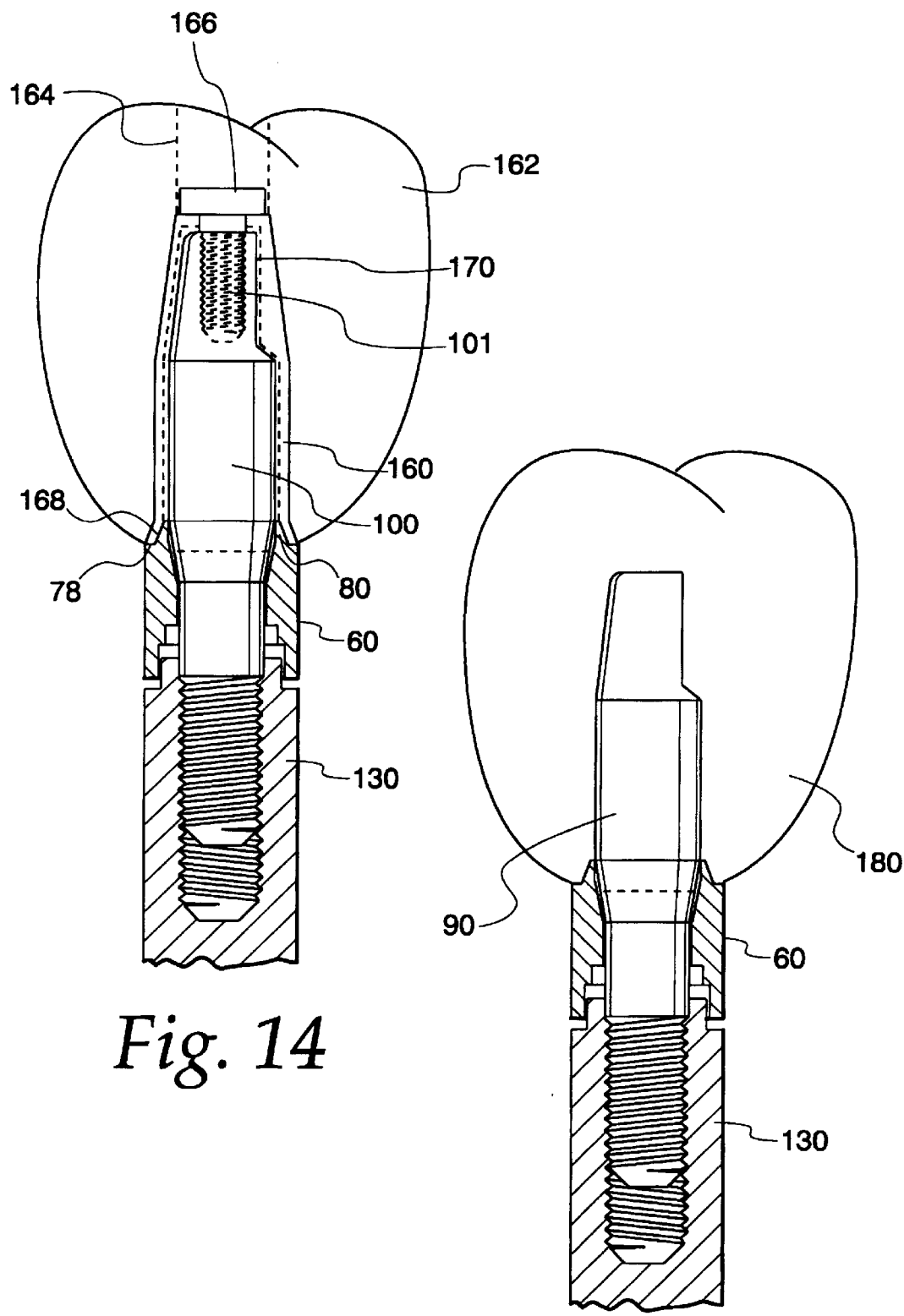
FIG. 14 illustrates the assembly of FIG. 11 with a prosthetic tooth mounted on a gold cylinder that is attached to the post.
FIG. 15 illustrates a two-piece assembly with a prosthetic tooth directly attached to the post.

FIG. 14 illustrates a cylinder 160 on which a prosthetic tooth 162 is permanently mounted. The prosthetic tooth 162 has a hole 164 at its upper end allowing a screw 166 to pass therethrough and connect the cylinder 160 to the second part 100 via the threaded bore 101. The cylinder 160 has a lower surface 168 which abuts the shoulder 78 of the first part 60. The interior surface of the cylinder 160 has a flat surface 170 that engages the flattened surface 108 of the second part 100. Thus, the cylinder 160 cannot rotate on the second part 100. Alternatively, the lower region of the cylinder 160 adjacent to the lower surface 168 could have a series of flats that could mate with a series of flats on the externally tapered region 80 of the first part 60 for resisting rotation.

FIG. 15 illustrates the second part 90 of FIGS. 8A–8B mounted on the first part 60. The surface of the second part 90 has been prepared to receive cement and connect the second part 90 to an artificial tooth 180. The artificial tooth 180 may be made of an acrylic such that the clinician can modify it to fit precisely in the patient's mouth. The artificial tooth 180 can be a permanent tooth, or it may be attached to the second part 90 via a temporary cement such that it is a temporary dentition.

FIG. 16a is a detailed view of the first part 60 showing the corners 70 and the anti-rotational structures 68 placed thereon. Because of the tolerances in the boss of the implant and the socket, these two-pieces never fit tightly within each other. Therefore, there is always a slight rotation between the parts. Typically, when a screw holds down an abutment, the torque is used to produce tension in the screw as its threads engage the implant. In the present invention, the torque on the second part is resisted by the friction at the engaged locking tapers of the first and second parts and by the tension produced by the engaging threads. Thus, the tension in the second part is typically less (because of the friction at the locking tapers that the torque overcomes) which increases the likelihood that the first part may loosen on the implant. One option is to decrease the cross-sectional area of the second part at a neck which increases the stress and increases the strain to hold the pieces tightly together. The second part 30 in FIG. 2 has such a neck between the threaded stem 32 and the male locking taper 38.

Figure 16E:
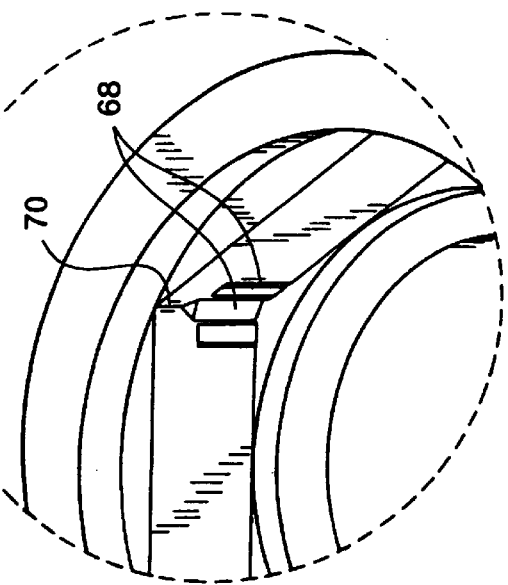

Alternatively, anti-rotational structures 68 can be used that make contact with sidewalls of the hexagonal boss of the implant at its corners to prevent rotation of the implant in the socket 66. These anti-rotational structures 68, as shown in FIG. 16a, are essentially shims located at the corners 70. Alternatively, the anti-rotational structures 68 can be removed somewhat from the corners 70, as is shown in FIG. 16b. Thus, they do not have to be located directly in the corners 70.

Figure 16C:
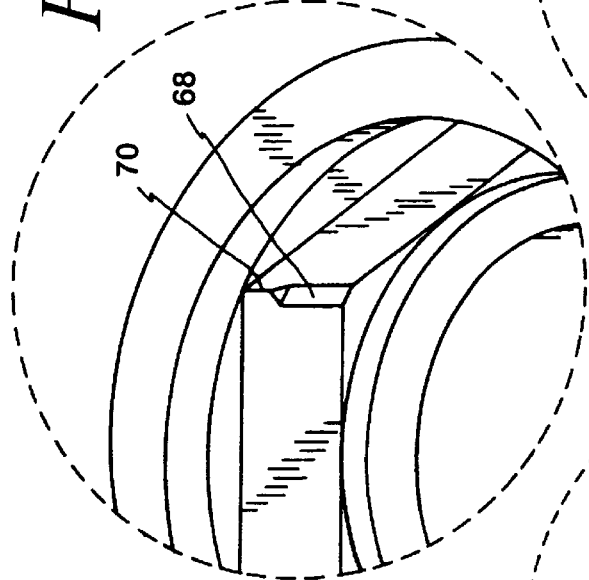

FIG. 16c illustrates the anti-rotational structures 68 being a corner block as opposed to being shims. The corner blocks come into firm contact with the hexagonal boss of the implant at the corners of the implants. The corner blocks are dimensioned so that opposite pairs of the blocks will squeeze the hexagonal boss between them to hold the first part 60 tightly on the implant.

Figure 16D:
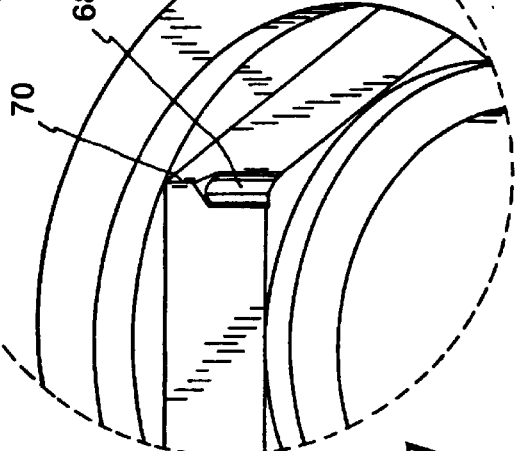
Figure 16B:
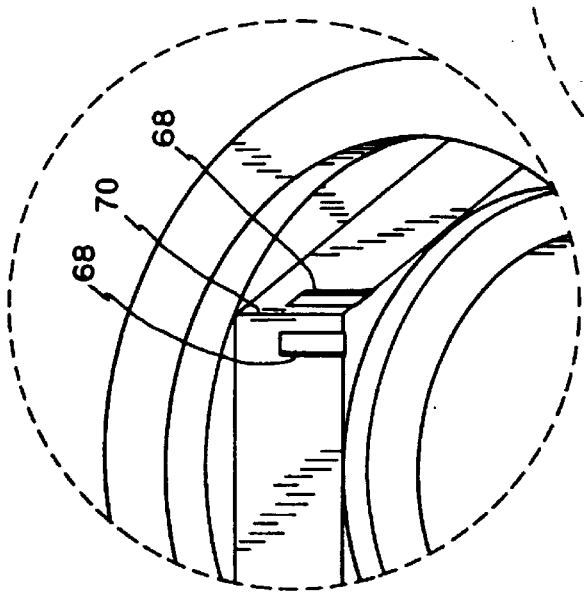

FIG. 16d shows anti-rotational structures 68 at the corners 70 which have the squeezing effect from the corner blocks as described above with reference to FIG. 16c. Additionally, the anti-rotational structures 68 have a shim-type structure which enhances the contact of anti-rotational structures 68 with the sides of the boss of the implant.

FIG. 16e shows an anti-rotational structure 68 in still another embodiment. Here, a corner block is in the corner 70 and shims are positioned outside the corner.

Figure 16F:
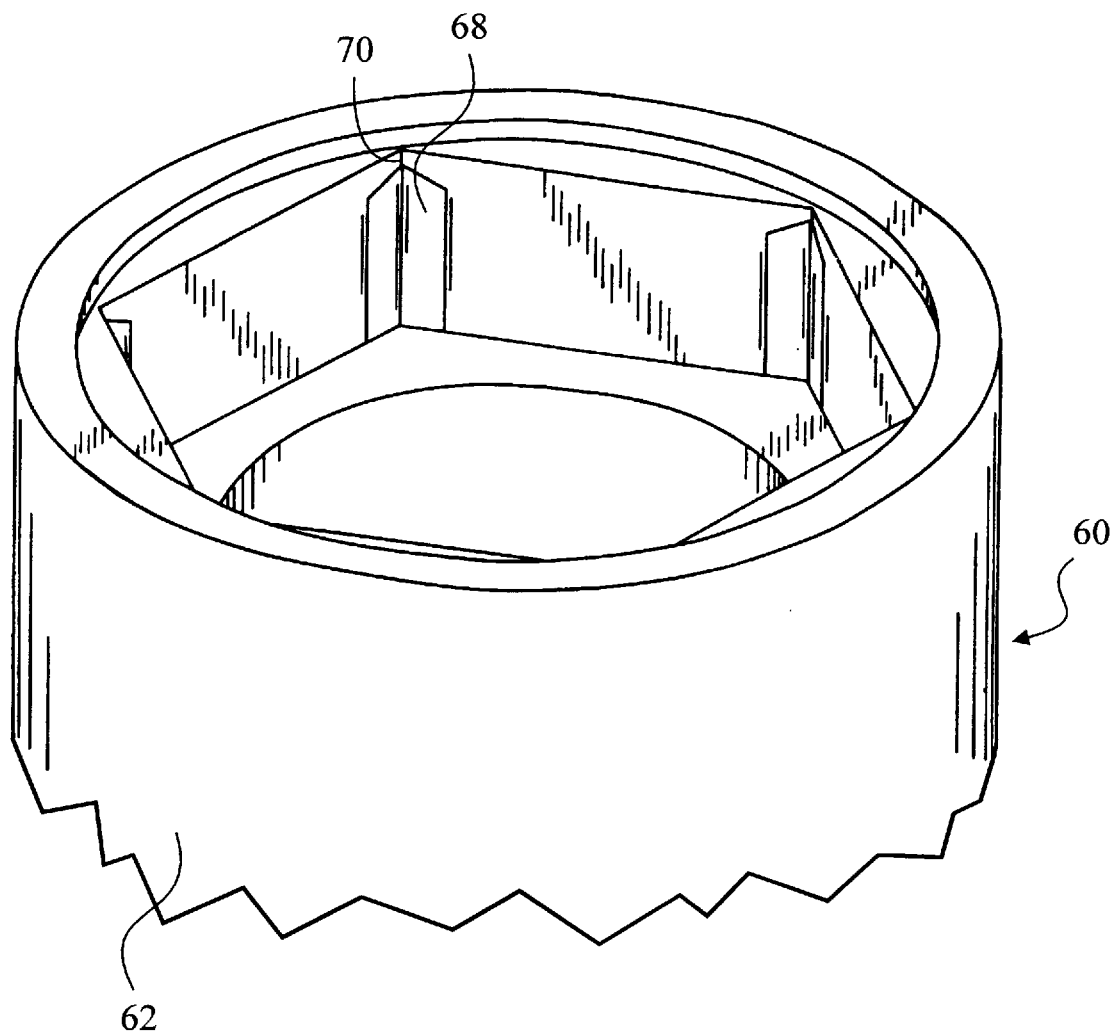

FIG. 16f shows a preferred embodiment of the invention which includes modified anti-rotational structures 68 to facilitate a smooth entrance of the hexagonal boss into the socket while still providing an anti-rotational effect. The improvement can best be observed by comparing the anti-rotational structures shown in FIG. 16f to those shown in FIG. 16a. Referring to FIG. 16a, it is noted that the corner anti-rotational structures 68 have upper edges which are substantially parallel to and spaced below the upper edge of the socket. Upon initial insertion and until encountering the upper edge of the corner anti-rotational structures 68, the hexagonal boss fits within the socket with the same degree of rotational looseness as encountered in the prior art. As the boss of the implant is inserted further into the socket, it encounters an abrupt "tightening" of fit along the upper edge of the corner anti-rotational structures 68. The embodiment shown in FIG. 16f facilitates entry of the boss into the socket by angling the upper edges of each corner shim pair relative to the upper edge of the socket. Specifically, the top edges of each shim pair are angled toward each other and toward the upper edge of the socket so that they meet at an apex near the upper end of a corner of the socket. As the boss is inserted into the socket, it initially encounters the same degree of rotational looseness as in the prior art, but quickly reaches the apexes of the angled shim pairs. As the boss of the implant penetrates further into the socket, the sidewalls of the boss contact the ends of the angled upper edges of the anti-rotational structures nearest the corners of the socket. Then, as the boss is further inserted into the socket, the sidewalls gradually come into contact with progressively increasing surface areas of the anti-rotational structures until the anti-rotational structures are in full contact with the boss and achieve the full anti-rotational effect. It may be noted that while the improvement of FIG. 16f has been described in relation to FIG. 16a, the same type of improvement may be achieved by angling the upper edges of the anti-rotational structures 68 in other embodiments such as those shown in FIGS. 16b, 16d, and 16e.

While the present invention has been described with reference to one or more particular embodiments those skilled in the art will recognize that many changes may be made thereto without departing from the spirit and scope of the present invention. Each of these embodiments and obvious variations thereof is contemplated as falling within the spirit and scope of the claimed invention.

What is claimed is:

1. The combination of a dental implant and an abutment, said implant for integrating with living jawbone and including a threaded bore and a boss protruding away from an upper portion thereof for engaging said abutment, said abutment comprising:

a first part having an upper end, a lower end, a central axis, and a bore extending therethrough along said central axis, said first part having adjacent to said lower end a socket for receiving said boss of said implant, a portion of said bore being defined by a surface that tapers inwardly toward said central axis in a direction toward said lower end at a predetermined angle, said first part including an annular shoulder positioned below said upper end for supporting a dental prosthesis, said first part diminishing in cross-section from said shoulder to said upper end; and an elongated second part for extending through said bore of said first part, said second part including a threaded portion for engaging said threaded bore of said implant and a post protruding substantially above said upper end of said first part, said second part including an outer surface with a tapered portion that tapers at an angle substantially the same as said predetermined angle for engaging said tapered surface of said first part, said post engaging the wall defining said bore immediately adjacent to said upper end of said first part.

2. The combination of claim 1, wherein said shoulder separates first and second regions of said first part, said first region being adjacent to said implant and flaring outwardly from said central axis in a direction away from said lower end, said second region flaring inwardly toward said central axis in a direction toward said upper end.

3. The combination of claim 1, wherein said predetermined angle is in the range from about 5° to about 20° for providing a locking taper between said first and second parts.

4. The combination of claim 1, wherein said post includes a threaded hole for receiving a screw to attach a component onto said second part.

5. The combination of claim 4, further including an impression coping fitting over said post and being attached thereon by a screw engaging said threaded hole in said post.

6. The combination of claim 4, further including a healing cap fitting over said post and being attached thereon by a screw engaging said threaded hole in said post.

7. The combination of claim 4, further including a cylinder fitting over said post and being attached thereon by a screw engaging said threaded hole in said post, said cylinder for holding a permanent denition.

8. The combination of claim 1, wherein said post includes a flat surface for non-rotationally engaging components attached on said second part.

9. The combination of claim 1, wherein said post includes a recessed surface to be engaged by a tool for rotating said second part.

10. The combination of claim 1, wherein said socket and said boss have a non-round shape to resist the rotation of said abutment around said implant, said socket further including anti-rotational structure to resist the turning of said first part on said implant.

11. The combination of claim 10, wherein said anti-rotational structure includes a shim-like structure.

12. The combination of claim 10, wherein said anti-rotational structure includes a block-like structure.

13. The combination of claim 1, further including an artificial tooth attached on said post.

14. The combination of claim 1, wherein said socket is a portion of said bore.

15. The combination of claim 1, wherein said first part has an exterior surface for engaging soft tissue overlying said jawbone with a portion thereof being non-round.

16. The combination of claim 1, wherein said post protrudes above said first part by a distance that is larger than the height of said first part.

17. The combination of claim 1, wherein said post protrudes above said first part by a distance that is at least as large as approximately the length of said second part below said upper end of said first part.

18. The combination of claim 1, wherein said threaded portion is a threaded stem integral with said second part.

19. The combination of a dental implant and an abutment, said implant for integrating with living jawbone and including a boss protruding away from an upper portion of said implant for engaging said abutment and a threaded bore, said abutment comprising:

a first part having an upper end, a lower end, a central axis, and a bore extending therethrough along said central axis, said bore including adjacent to said lower end a socket including anti-rotational structure for receiving said boss of said implant, a portion of said bore being defined by a surface that tapers inwardly toward said central axis in a direction toward said lower end at a predetermined angle being between about 5° and 20°, said first part having a shoulder facing away from said implant for engaging another component; and an elongated second part for extending through said bore of said first part, said second part including a threaded stem for engaging said threaded bore of said implant and a post protruding above said upper end of said first part, said second part including an outer surface with a tapered portion tapering at an angle substantially the same as said predetermined angle for engaging said surface of said first part and providing a locking engagement between said first and second parts, said second part having a flat surface for engaging said another component and a threaded hole for receiving a screw for attaching said another component thereon.

20. The combination of claim 19, further including an impression coping fitting over said post and being attached thereon by a screw engaging said threaded hole in said post, said impression coping being said another component.

21. The combination of claim 19, further including a healing cap fitting over said post and being attached thereon by a screw engaging said threaded hole in said post, said healing cap being said another component.

22. The combination of claim 19, further including a cylinder fitting over said post and being attached thereon by a screw engaging said threaded hole in said post, said cylinder for holding a permanent denition, said cylinder being said another component.

23. The combination of claim 19, further including an artificial tooth attached on said post.

24. The combination of claim 19, wherein said first part has an exterior surface for engaging soft tissue overlying said jawbone with a portion thereof being non-round.

25. An abutment for attaching to a dental implant embedded in living jawbone and having a fitting at its upper end, said abutment comprising:

a first part having an upper end, a lower end, a central axis, and a bore extending therethrough along said central axis, said first part having adjacent to said lower end a interlocking fitting for mating with said fitting of said implant, said bore being defined in part by a surface that tapers inwardly toward said central axis in the direction of said lower end at a predetermined angle; and an elongated second part for extending through said bore of said first part, said second part including a threaded stem for engaging said threaded bore of said implant and a post protruding substantially above said upper end of said first part, said second part including an outer surface with a tapered portion that tapers at an angle substantially the same as said predetermined angle, said tapered portion lockingly engaging said surface of said first part to hold said first and second part together, said post further having a non-round cross-sectional shape for non-rotationally mating with a dental prosthesis.

26. The abutment of claim 25, wherein said post includes a threaded hole for receiving a screw to attach a component onto said second part.

27. The abutment of claim 25, wherein said post includes a flat surface for non-rotationally engaging components attached on said second part.

28. The abutment of claim 25, wherein said socket includes anti-rotational structure to resist the turning of said first part on said implant.

29. The abutment of claim 25, wherein said first part has an exterior surface for engaging soft tissue overlying said jawbone with a portion thereof being non-round.

30. The abutment of claim 25, wherein said threaded portion is a threaded stem integral with said second part.

31. An abutment for holding a dental prosthesis that is to be attached to a dental implant embedded in living jawbone, said abutment comprising:

a first part having a bore extending therethrough along said central axis, said first part having means for non-rotationally mating with said implant and an internal surface that tapers inwardly toward said central axis, said first part including an annular shoulder positioned below said upper end for supporting a dental prosthesis, said first part diminishing in cross-section from said shoulder to said upper end; and an elongated second part for extending through said bore of said first part, said second part including a threaded stem for threadably engaging said threaded bore of said implant and a post protruding above said first part, said second part including an outer surface with a tapered portion that tapers at an angle substantially the same as said predetermined angle, said tapered portion engaging said internal surface of said first part in response to said threaded stem being threadably engaged in said threaded bore of said implant, said post engaging the wall defining said bore immediately adjacent to said upper end of said first part, said post further having a non-round cross-section shape for non-rotationally mating with said dental prosthesis.

32. The abutment of claim 31, wherein said post includes a threaded hole for receiving a screw to attach a component onto said second part.

33. The abutment of claim 31, wherein non-round cross section of said post is defined by a flat surface for non-rotationally engaging components attached on said second part.

34. The abutment of claim 31, wherein said mating means is a socket.

35. The abutment of claim 34, said mating means includes anti-rotational structure to resist the turning of said first part on said implant.

36. The abutment of claim 31, wherein said first part has an exterior surface for engaging soft tissue overlying said jawbone with a portion thereof being non-round.

37. The abutment of claim 31, wherein said tapered portion of said bore and said tapered outer surface are angled between 5° to 20° to provide a locking engagement between said first and second parts.

38. The abutment of claim 31, wherein said shoulder is in a plane that is generally perpendicular to said central axis.

39. An abutment for holding a dental prosthesis that is to be attached to a dental implant embedded in living jawbone, said abutment comprising:

a first part having a bore extending therethrough along said central axis, said first part having means for non-rotationally mating with said implant and an internal surface that tapers inwardly toward said central axis, said first part further having an annular shoulder facing away from dental implant for engaging a dental prosthesis, at least a portion of said shoulder being below said upper end such that said first part is capable of providing lateral support to said dental prosthesis, said first part diminishing in cross-section from said shoulder to said upper end; and an elongated second part for extending through said bore of said first part, said second part including a threaded stem for threadably engaging said threaded bore of said implant and a post protruding above said first part, said second part including an outer surface with a tapered portion that tapers at an angle substantially the same as said predetermined angle, said tapered portion engaging said internal surface of said first part in response to said threaded stem being threadably engaged in said threaded bore of said implant, said post engaging the wall defining said bore immediately adjacent to said upper end of said first part.

40. The abutment of claim 39, further including an artificial tooth attached on said post and on said shoulder.

41. The abutment of claim 39, wherein said shoulder has an annular shape.

42. The abutment of claim 39, wherein said shoulder is in one plane.

43. A kit of dental components comprising:

an abutment including a first part having a bore extending therethrough along said central axis, said first part having means for non-rotationally mating with said implant and an internal surface that tapers inwardly toward said central axis, said abutment further including an elongated second part for extending through said bore of said first part, said first part including a shoulder positioned below said upper end for supporting a dental prosthesis, said second part including a threaded stem for threadably engaging a threaded bore of a dental implant and a post protruding above said first part, said second part including an outer surface with a tapered portion that tapers at an angle substantially the same as said predetermined angle, said tapered portion frictionally engaging said internal surface of said first part in response to said threaded stem being threadably engaged in said threaded bore of said implant, said post portion engaging the wall defining said bore immediately adjacent to said upper end of said first part;

a healing cap for placement over said post including means for attaching said healing cap to said post; and an impression coping for placement over said post including means for attaching said impression coping to said post.

44. The kit of claim 43, wherein said second part includes a threaded hole and said means for attaching said healing cap includes a screw engaging said threaded hole.

45. The kit of claim 43, wherein said second part includes a threaded hole and said means for attaching said impression coping includes a screw engaging said threaded hole.

46. The kit of claim 45, wherein said screw is elongated and said impression coping is a pick-up coping.

47. The kit of claim 45, wherein said screw is a wide-head screw and said impression coping is a transfer coping.

48. The kit of claim 43, wherein said shoulder on said abutment further supports said impression coping.

49. The kit of claim 43, wherein said shoulder on said abutment further supports said healing cap.

50. An abutment for attaching to a dental implant embedded in living jawbone and having a fitting at its upper end, said abutment comprising:

a tubular first part having an upper end, a lower end, a central axis, and a bore extending therethrough along said central axis, said tubular first part having adjacent to said lower end an interlocking fitting for mating with said fitting of said implant, said bore including a tapered portion, said tubular first part having a height measured between said lower end and said upper end, said first part including a shoulder positioned below said upper end for supporting a dental prosthesis; and an elongated second part for extending through said bore of said first part, said second part including a threaded stem for engaging said threaded bore of said implant and a post protruding above said upper end of said first part by a distance that is larger than said height of said tubular first part, said elongated second part including a tapered outer surface for engaging said tapered portion of said bore.

51. The abutment of claim 50, wherein said tapered portion of said bore and said tapered outer surface of said elongated second part are angled between 5° to 20° to provide a locking engagement between said first and second parts.

52. The abutment of claim 50, wherein said shoulder separates first and second regions of said first part, said first region being adjacent to said implant and flaring outwardly from said central axis in a direction away from said lower end, said second region flaring inwardly toward said central axis in a direction toward said upper end.

53. An abutment for attaching to a dental implant embedded in living jawbone and having a fitting at its upper end, said abutment comprising:

a tubular first part having an upper end, a lower end, a central axis, and a bore extending therethrough along said central axis, said tubular first part having adjacent to said lower end an interlocking fitting for mating with said fitting of said implant, said bore including a tapered portion, said first part including a shoulder positioned below said upper end for supporting a dental prosthesis; and an elongated second part for extending through said bore of said first part, said second part including a threaded stem for engaging said threaded bore of said implant and a post protruding above said first part by a distance that is at least as large as approximately the length of said second part below said upper end of said first part, said elongated second part including a tapered outer surface for engaging said tapered portion of said bore.

54. The combination of a dental implant, an abutment, and an impression coping, said implant for integrating with living jawbone and including a threaded bore and a boss protruding away from an upper portion thereof for engaging said abutment, said abutment comprising:

a first part having an upper end, a lower end, a central axis, and a bore extending therethrough along said central axis, said first part having adjacent to said lower end a socket for receiving said boss of said implant, a portion of said bore being defined by a surface that tapers inwardly toward said central axis in a direction toward said lower end at a predetermined angle, said first part including a shoulder positioned below said upper end for supporting a dental prosthesis; and an elongated second part for extending through said bore of said first part, said second part including a threaded portion for engaging said threaded bore of said implant and a post protruding substantially above said upper end of said first part, said second part including an outer surface with a tapered portion that tapers at an angle substantially the same as said predetermined angle for engaging said tapered surface of said first part, said post engaging the wall defining said bore immediately adjacent to said upper end of said first part and including a threaded hole for receiving a screw to attach a component onto said second part; and wherein said impression coping fits over said post and is attached thereon by a screw engaging said threaded hole in said post.

* * * * *